(12) United States Patent
Godoy

(10) Patent No.: US 7,275,536 B2
(45) Date of Patent: Oct. 2, 2007

(54) DEVICE FOR VARYING THE LENGTH OF A STRAP ON A MASK FOR AQUATIC ACTIVITIES

(75) Inventor: Carlos Godoy, Genoa (IT)

(73) Assignee: Cressi-Sub S.p.A., Genoa (IT)

( * ) Notice: Subject to any disclaimer, the term of this patent is extended or adjusted under 35 U.S.C. 154(b) by 0 days.

(21) Appl. No.: 10/934,291

(22) Filed: Sep. 3, 2004

(65) Prior Publication Data

US 2005/0045176 A1    Mar. 3, 2005

(30) Foreign Application Priority Data

Sep. 3, 2003    (IT)    ................ FI2003U0082 U

(51) Int. Cl.
*A62B 9/04*    (2006.01)
*B63C 11/02*    (2006.01)
*A41F 1/00*    (2006.01)
*A61F 9/02*    (2006.01)

(52) U.S. Cl. .................. 128/201.27; 128/202.27; 2/428; 2/452; 24/625

(58) Field of Classification Search ............. 24/585.11, 24/170, 191, 625; 128/206.21, 207.11, 201.11, 128/201.26, 201.27, 202.27, 898; 2/248, 2/426, 430, 429, 452, 428; 351/43; 405/185, 405/188, 187

See application file for complete search history.

(56) References Cited

U.S. PATENT DOCUMENTS

| | | | |
|---|---|---|---|
| 4,171,543 A | 10/1979 | Cressi | ............................ 2/428 |
| 4,607,398 A * | 8/1986 | Faulconer | ...................... 2/452 |
| D324,589 S | 3/1992 | Dagnino | ........................ D29/9 |
| 5,181,280 A * | 1/1993 | Zachry, Jr. | ...................... 2/452 |
| 5,467,508 A * | 11/1995 | Feng | ........................ 24/68 SK |
| 5,638,552 A * | 6/1997 | Fujima | ............................ 2/428 |
| 5,657,493 A * | 8/1997 | Ferrero et al. | ................. 2/428 |
| 5,956,778 A * | 9/1999 | Godoy | ............................ 2/428 |
| 6,131,246 A * | 10/2000 | Paulson et al. | ......... 24/265 BC |
| 6,272,693 B1 | 8/2001 | Godoy | ............................ 2/430 |
| 6,350,030 B2 * | 2/2002 | Fujima | ........................ 351/43 |
| 6,446,272 B1 * | 9/2002 | Lee | ................................ 2/428 |
| 6,640,347 B2 * | 11/2003 | Fukasawa | ....................... 2/428 |
| 6,718,560 B2 | 4/2004 | Godoy | ............................ 2/435 |
| 6,845,521 B2 * | 1/2005 | Takeshi et al. | ................. 2/452 |
| D522,562 S | 6/2006 | Godoy | ...................... D16/311 |

* cited by examiner

*Primary Examiner*—Justine R. Yu
*Assistant Examiner*—Annette Dixon
(74) *Attorney, Agent, or Firm*—Pollack, P.C.

(57) ABSTRACT

A device is disclosed for adjusting the length of a strap on a mask for aquatic activities. The mask comprises a frame for supporting one or more lenses and a plurality of fork-shaped portions extending from either side of the frame. Each portion contains a pivot about which a portion of a strap end is wrapped, the portion having a plurality of stop ribs on one side. The adjustment device comprises a stop lever housed in each portion and a tooth extending from the lever for engaging one of the ribs. The lever has a substantially U-shaped member and a tongue extending from the base of the member such that the tongue is coplanar with and cantilevered in the lever. On a side opposite the tooth, a head extends from the tongue, against which a wedge-shaped portion of a button abuts, sliding with respect to the fork-shaped portion on a plane generally parallel to the U-shaped member. When the button is pressed, the head slides away from the member, lifting the tongue and, thereby, disengaging the tooth from the rib.

7 Claims, 3 Drawing Sheets

DEVICE FOR VARYING THE LENGTH OF A STRAP ON A MASK FOR AQUATIC ACTIVITIES

FIELD OF THE INVENTION

The present invention relates generally to equipment for use in limited oxygen environments and, more particularly, to a device for ensuring sealing engagement between a scuba diver's mask and head, or the like.

BACKGROUND OF THE INVENTION

Scuba diving masks typically comprise a frame to which one or two lenses are attached by way of a watertight seal. A soft facepiece extends from an edge of the frame to create a seal with a diver's face. A flexible strap is also provided, the ends of which are connected to opposing sides of the frame. The length of the strap is usually adjustable so as to exert sufficient tension and, thereby, ensure relatively stable positioning of the facepiece on the diver's face and adequate watertightness.

The length of the strap is usually adjusted using a buckle. Although useful, buckles have been found impractical, especially when the diver is wearing gloves, or has cold and/or wet hands. Another common approach is to provide fasteners that enable the length of the strap to be varied without the necessity of having the diver take off his or her mask. One solution has been to provide a strap with ends that wrap around pivots on fork-shaped side portions of the mask. The strap has transverse stop ribbing operatively engaged with a stop tooth projecting from a lever which is, in turn, pressed elastically against the ribs. Upon overcoming the elastic resistance created, the lever may then be raised by the user, thereby, enabling the strap to slide to a new position, without removing the mask from the user's face. The elastic resistance is provided by a spring in some arrangements, whereas in others the lever itself is utilized, the lever being flexed in order to detach the tooth from the strap and, thereby, enable the latter to slide. Although the foregoing approaches do not require that the mask be removed, adjustment of the strap has remained difficult and uncomfortable, especially when done with cold and/or wet hands. Moreover, strap adjustment cannot be done while the diver is wearing gloves since a finger tip is needed to lift the lever attached to the stop tooth which engages the strap's ribbing.

In another arrangement, a compact device is provided for varying the length of a strap suitable for use on swimming goggles. This device comprises a stop lever and a tooth extending from the lever. The lever engages a rib on the strap which is wrapped about an underlying pivot and integrally attached to a side portion of the goggles' frame. The lever includes a first arm, preferably in the form of a fork, with a first end pivotally connected to the side portion and a second end abutting the bottom of a seat in the side portion. In addition, a second arm is provided from which the tooth extends transversely, the second arm having a free first end for operation and a second end rigidly connected to the second end of the first arm. The second arm is desirably a tongue extending cantilevered from and coplanar with the fork that forms the first arm. The second arm also has a raised portion at its free end that may be used to lift the tongue, disengage the transverse tooth from the rib on the strap, and thereby allow the arm to slide. While this arrangement is beneficial, the stop lever has been found relatively difficult to operate.

Another drawback of this approach is that the lever has been found difficult to operate.

OBJECTS AND SUMMARY OF THE INVENTION

It is, therefore, an object of the present invention to provide a device for varying the length of a scuba diving mask strap that can be operated more easily and comfortably than conventional arrangements, even when wearing gloves.

According to one aspect of the present invention, a device is provided for adjusting the length of a strap on a scuba diving mask. The mask comprises a frame for supporting a lens and has a plurality of fork-shaped portions extending from either side of the frame. Each portion contains a pivot about which a portion of the strap end is wrapped, the strap portion having a plurality of transverse stop ribs on one side. The device includes a stop lever housed in each of the fork-shaped portions and a tooth extending from the lever for engaging one of the ribs. Preferably, the lever has a substantially U-shaped member and a tongue extending from the base of the member such that the tongue is coplanar with and cantilevered in the lever. The tooth also extends transversely from the tongue. On a side opposite the tooth, a head extends from the tongue, against which a wedge-shaped portion of a button abuts, sliding with respect to the fork-shaped portion in a plane generally parallel to the U-shaped member. When the button is pressed, the head slides away from the member, thereby lifting of the tongue and disengaging the tooth from the stop rib.

According to another aspect of the present invention, a device is provided for adjusting the length of a strap on a scuba diving mask. The mask comprises a frame for supporting a plurality of lenses and has a plurality of fork-shaped portions extending from either side of the frame. Each portion contains a pivot about which a portion of the strap end is wrapped, the strap portion having a plurality of transverse stop ribs on one side. The device includes a stop lever housed in each of the fork-shaped portions and a tooth extending from the lever for engaging one of the ribs. Preferably, the lever has a substantially U-shaped member and a tongue extending from the base of the member such that the tongue is coplanar with and cantilevered in the lever. The tooth also extends transversely from the tongue. On a side opposite the tooth, a head extends from the tongue, against which a wedge-shaped portion of a button abuts, sliding with respect to the fork-shaped portion in a plane generally parallel to the U-shaped member. When the button is pressed, the head slides away from the member, thereby lifting of the tongue and disengaging the tooth from the stop rib.

BRIEF DESCRIPTION OF THE DRAWINGS

A specific, illustrative device for adjusting the length of a scuba diving mask strap or the like, in accordance with the present invention, is described below with reference to the accompanying drawings, in which.

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1:
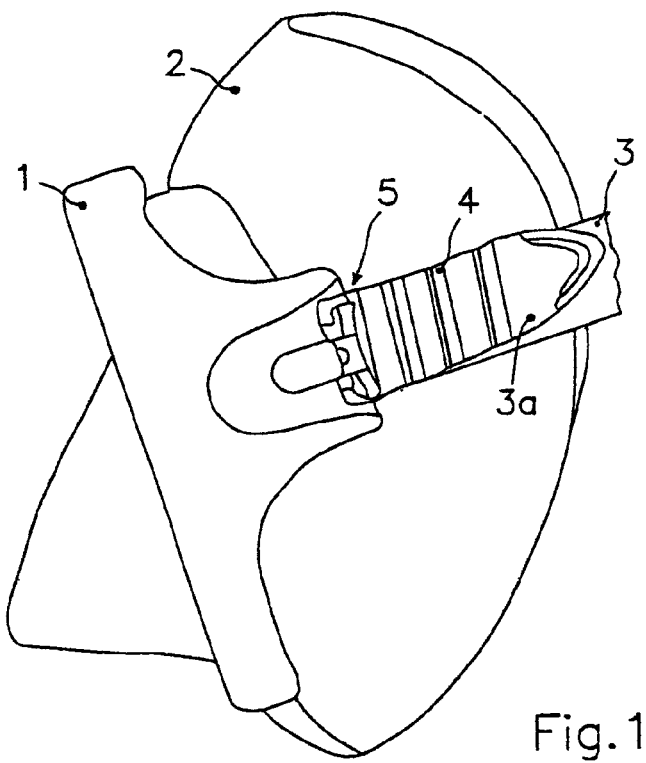
FIG. 1 is a side view of a scuba diving mask, in accordance with one aspect of the present invention.

Referring now to the drawings and, more particularly, to FIGS. 1–6, there is shown generally a specific, illustrative device for adjusting the strap length of a scuba diving mask 1, in accordance with the present invention. According to one embodiment, illustrated generally in FIG. 1, the mask includes a frame mounting one or two lenses (not shown) in a watertight seal. The frame also mounts a facepiece 2 constructed of a relatively soft material, the facepiece extending from an edge of the frame suitably for conforming the mask to a diver's face and ensuring a watertight seal with the diver's face. More specifically, the seal is achieved by adjusting the tightness of the mask against his or her face using a belt or strap 3 that wraps about the diver's head.

The strap preferably has a set of transverse ribs 4 on one side of its terminal portions 3a, which engage a device for fastening and varying the length of the strap, indicated generally by the reference numeral 5.

Figure 2:
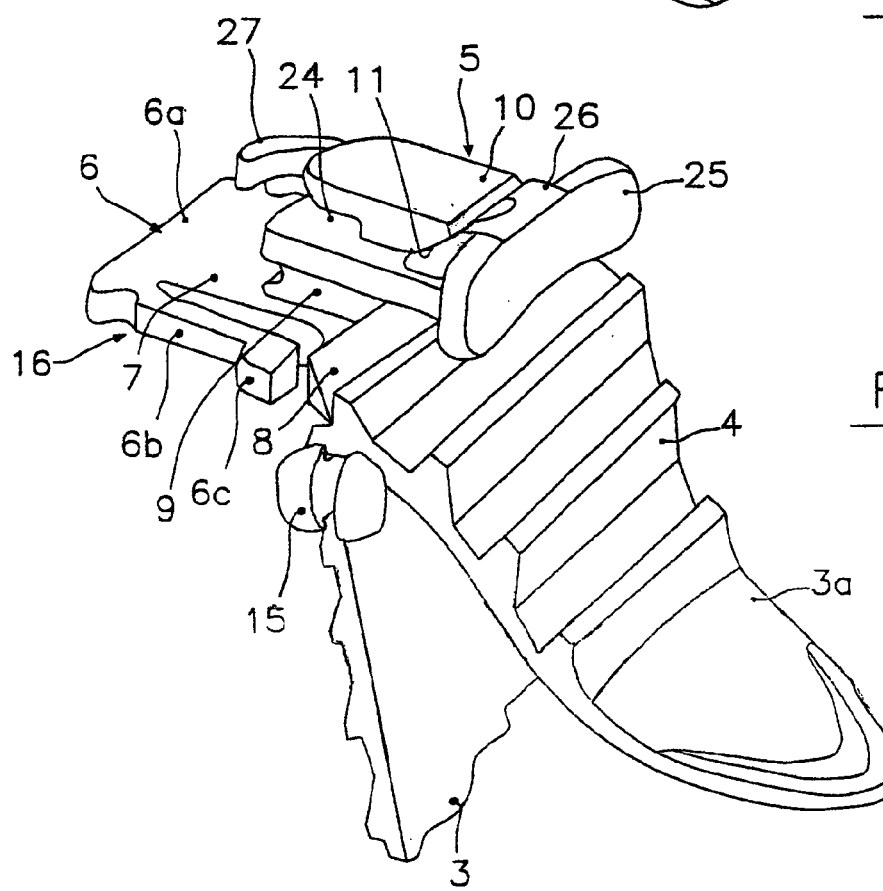
FIG. 2 is a perspective view of the device shown in FIG. 1.
Figure 3:
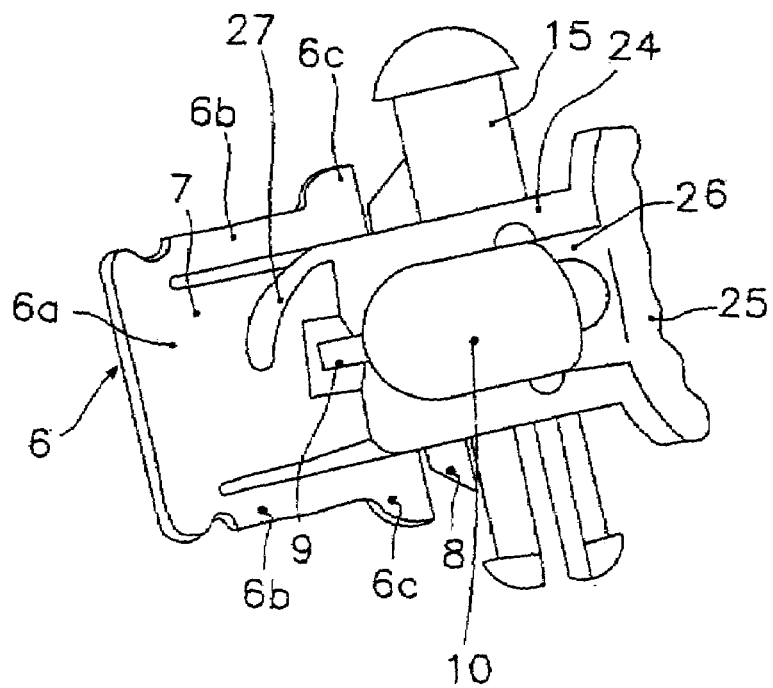
FIG. 3 is a plan view of the device shown in FIG. 1.

As best seen in FIGS. 2 and 3, fastening device 5 preferably comprises a first, substantially U-shaped member 6 that includes a base 6a and a pair of brackets 6b having expanded tips 6c that extend from the base, remaining coplanar thereto, and a tongue 7 extending from the base between the brackets in a position substantially coplanar with the brackets. A transverse tooth 8, in turn, projects from a free end of the tongue. The U-shaped member 6, the tongue 7 and corresponding tooth 8 constitute, collectively, an assembly of a stop lever 16 for the device, according to the present invention.

On a side opposite the transverse tooth, a column 9 is provided that extends from the tongue. The tongue is desirably enlarged at one end so as to form a head 10. On the head (which is on a side opposite base 6a of the U-shaped member 6) a surface 11 is provided that slopes generally toward the tongue.

Figure 4:
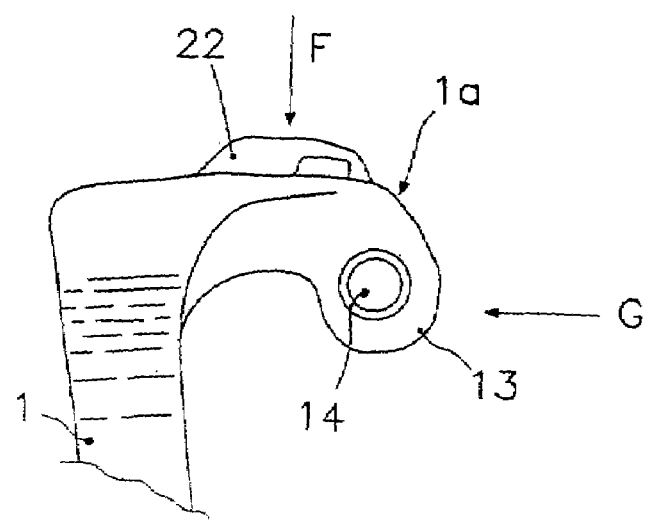
FIG. 4 is a top view of a scuba diving mask frame housing the device shown in FIG. 1.
Figure 5:
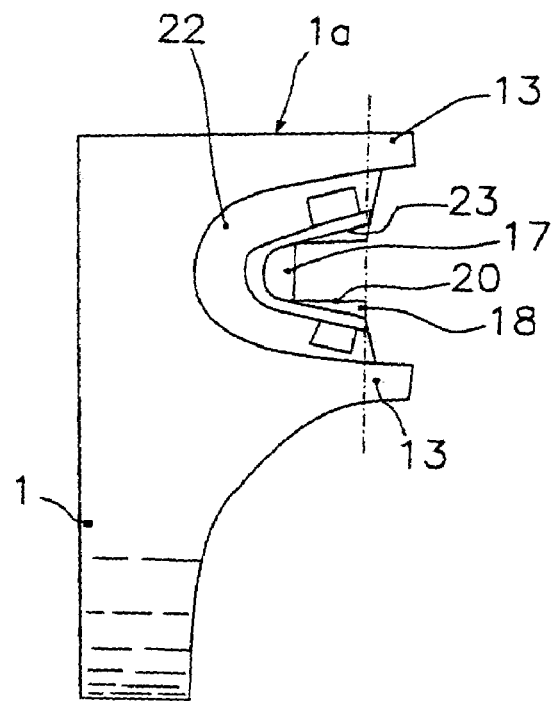
FIG. 5 is a side view of detail shown in FIG. 4, at arrow F.
Figure 6:
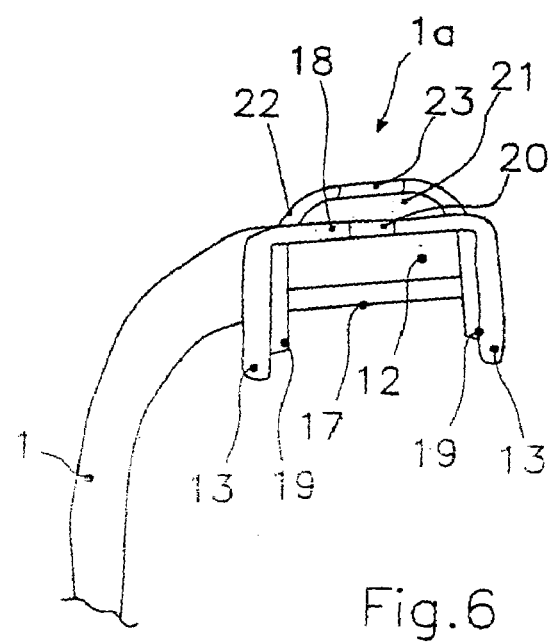
FIG. 6 is a rear view of detail shown in FIG. 4, at arrow G.

Turning now to FIGS. 4, 5 and 6, stop lever 16 is preferably mounted inside a seat 12 of a fork-shaped side portion 1a projecting from frame 1. In one embodiment, the side portion comprises a pair of fins 13, with a corresponding pair of coaxial holes 14, a pivot 15 snapingly secured in the holes, terminal portion 3a of the strap desirably being wrapped around the pivot.

First seat 12 comes between fins 13 and two substantially parallel walls 17 and 18 extending between them. Preferably, the depth of the first seat is such that base 6a of U-shaped member 6 abuts the bottom of the seat, and that expanded tips 6c on its brackets 6b abut ribbing 19 along the fins at the inlet to the seat. In this manner, once the U-shaped member 6 is snapped into the seat, it remains locked therein.

Wall 18, forming an outer side of the first seat and, hence, a longitudinal slot 20, is occupied by column 9 which extends from tongue 7. A second seat 21, located beyond the wall, is surrounded on the outside by a wall 22, a suitable longitudinal slot 23 lying above the slot and containing the column such that its enlarged end, or head 10, projects therefrom.

A plate 24, having one end 25 enlarged and in the shape of a button, projects from and is slidingly engaged about the column within seat 21. Between the button-shaped end or button 25 and head 10 situated at the end of the column, a sloping wall 26 is provided that corresponds with wall 11 under the head and slopes generally at the same angle. Pressing button 25 of the plate causes the plate to slide into the seat, thereby bringing sloping walls 26 and 11 in contact with one another. Since head 1 is integral with lever 16, which cannot slide within the seat, the head with its sloping wall 11 is forced to slide along sloping wall 26 of the button, and is lifted thereby. As head 10 rises, it, in turn, lifts tongue 7 and, consequently, causes the tooth 8 to be disengaged from rib 4 on the strap, thus enabling the strap to slide around pivot 15. To cause tooth 8 to return automatically and engage the rib when the pressure exerted on the button is released, plate 24 is forced elastically against the bottom of seat 21. In this connection, an arm 27 extends from an end of the plate opposite the button, the arm being bent over so as to form an arch and suitably for abutting the bottom of the seat, as it flexes under the pressure induced by sliding of the plate. When head 10 is consequently lowered and tooth 8 re-engages rib 4, the arm returns to its starting position. In order to prevent the plate from sliding out of the seat at the end of its return stroke, the plate desirably abuts column 9, about which it is installed. Preferably, the height of the column is designed so that minimal effort is needed to cause the plate to slide and, in turn, the head to rise.

According to one aspect of the present invention, a device is provided for adjusting the length of a strap on a scuba diving mask. The mask comprises a frame for supporting a plurality of lenses and has a plurality of fork-shaped portions extending from either side of the frame. Each portion contains a pivot about which a portion of the strap end is wrapped, the strap portion being formed with a plurality of transverse stop ribs on one side. The device includes a stop lever housed in each of the fork-shaped portions and a tooth extending from the lever for engaging one of the ribs. The lever has a substantially U-shaped member and a tongue extending from the base of the member such that the tongue is coplanar with and cantilevered in the lever. The tooth also extends transversely from the tongue. On a side opposite the tooth, a head extends from the tongue, against which a wedge-shaped portion of a button abuts, sliding with respect to the fork-shaped portion in a plane generally parallel to the U-shaped member. When the button is pressed, the head slides away from the member, thereby lifting of the tongue and disengaging the tooth from the stop rib. arm is bent over to form an arc and suitable for abutting against the bottom of the seat 21 as it flexes under the effect of the pressure induced by the sliding of the plate 24, then returning to its undeformed condition when the pressure is released and thus returning the button 25 to its initial position, when the head 10 is consequently lowered and the tooth 8 re-engages with a rib 4. To prevent the plate 24 from sliding out of its seat 21 at the end of its return stroke, it abuts against the column 9 around which it is installed.

It should be noted that the height of the column 9 is designed so that a minimal effort is needed to make the plate 24 slide and the head 10 rise.

Overall, the present invention advantageously provides both comfort and ease of use in varying the length of a strap on a mask for aquatic activities. The device is also easily adjusted without the necessity of first removing the mask, even when the diver is wearing gloves. These benefits are achieved by lifting the lever, which disengages the tooth from ribbing on the strap, not by acting directly on the strap, but rather using a tugging action which operates parallel to the movement that disengages the tooth as with conventional devices, and a button connected to the lever. In this manner, the device is much more readily accessible so that pressure can be exerted in a direction generally perpendicular to that of strap movement, i.e. substantially parallel to the plane in which the end of the strap lies.

Although the present invention is shown and described for use with a scuba diving mask, those skilled in the art will appreciate its application to other arrangements, giving consideration to the purpose for which the invention is intended. For instance, its application to swimming goggles is considered equivalently advantageous, within the spirit and scope of the present invention.

Various modifications and alterations to the present invention may be appreciated based on a review of this disclosure. These changes and additions are intended to be within the scope and spirit of the invention as defined by the following claims.

What is claimed is:

1. A device for varying the length of strap on a mask for aquatic activities, the mask comprising a frame for supporting a lens and a plurality of fork-shaped portions extending from either side of the frame, each portion having a pivot about which a portion of the strap end is wrapped, the strap portion having a plurality of transverse stop ribs on one side, wherein the device includes a stop lever housed in each of the fork-shaped portions and a tooth extending from the lever for engaging one of the ribs, the lever having a substantially U-shaped member and a tongue extending from the base of the member such that the tongue is coplanar with and cantilevered in the lever, the tooth extending transversely from the tongue; wherein, on a side opposite the tooth, a head extends from the tongue, against which a wedge-shaped portion of a button abuts, sliding with respect to the fork-shaped portion in a plane generally parallel to the U-shaped member, whereby, when the button is pressed, the head slides away from the member, thereby lifting of the tongue and disengaging the tooth from the rib.

2. The device set forth in claim 1, wherein each of the fork-shaped portions has a first seat for snapingly securing the substantially U-shaped member and a second seat over the first seat for slidingly housing a plate extending from the button, the head being formed at an end of a column extending from the tongue and passing through the second seat, such that the head projects above the second seat.

3. The device set forth in claim 2, wherein the button is elastically biased against the bottom of the second seat.

4. The device set forth in claim 3, wherein a curved arm extends from the sliding plate of the button and flexibly abuts the bottom of the second seat.

5. The device set forth in claim 2, wherein the plate is arranged about the column, sliding generally perpendicularly relative to and abutting the column, thereby being prevented from sliding out of the second seat.

6. The device set forth in claim 2, wherein the fork-shaped portion includes a plurality of relatively parallel fins with coaxial holes for supporting the pivot, the first and second seat extending one above the other, between the fins and delimited by three substantially parallel walls, a plurality of which have a slot for housing the column on the tongue.

7. A device for varying the length of strap on a mask for aquatic activities, the mask comprising a frame for supporting a plurality of lenses and a plurality of fork-shaped portions extending from either side of the frame, each portion having a pivot about which a portion of the strap end is wrapped, the strap portion having a plurality of transverse stop ribs on one side, wherein the device includes a stop lever housed in each of the fork-shaped portions and a tooth extending from the lever for engaging one of the ribs, the lever having a substantially U-shaped member and a tongue extending from the base of the member such that the tongue is coplanar with and cantilevered in the lever, the tooth extending transversely from the tongue; wherein, on a side opposite the tooth, a head extends from the tongue, against which a wedge-shaped portion of a button abuts, sliding with respect to the fork-shaped portion in a plane generally parallel to the U-shaped member, whereby, when the button is pressed, the head slides away from the member, thereby lifting of the tongue and disengaging the tooth from the rib.

* * * * *